United States Patent
Casper et al.

(10) Patent No.: US 9,750,918 B2
(45) Date of Patent: Sep. 5, 2017

(54) METHODS AND DEVICES FOR IMPROVING SLEEP PERFORMANCE IN SUBJECT EXPOSED TO LIGHT AT NIGHT

(71) Applicant: ZIRCLIGHT INC., Stoneham, MA (US)

(72) Inventors: Robert F. Casper, Toronto (CA); Shadab A. Rahman, Malden, MA (US)

(73) Assignee: Circadian Zirclight Inc., Stoneham, MA (US)

( * ) Notice: Subject to any disclaimer, the term of this patent is extended or adjusted under 35 U.S.C. 154(b) by 285 days.

(21) Appl. No.: 14/250,186

(22) Filed: Apr. 10, 2014

(65) Prior Publication Data
US 2014/0309482 A1 Oct. 16, 2014

Related U.S. Application Data

(60) Provisional application No. 61/810,985, filed on Apr. 11, 2013.

(51) Int. Cl.
*A61M 21/00* (2006.01)
*A61M 21/02* (2006.01)

(52) U.S. Cl.
CPC .......... *A61M 21/00* (2013.01); *A61M 21/02* (2013.01); *A61M 2021/005* (2013.01); *A61M 2205/50* (2013.01)

(58) Field of Classification Search
CPC .......... A61M 21/00; A61M 21/02; A61M 2021/005; A61M 2205/50
See application file for complete search history.

(56) References Cited

U.S. PATENT DOCUMENTS

| 5,402,190 A | * | 3/1995 | Waldman | G02C 5/001 351/159.63 |
| 2008/0065177 A1 | * | 3/2008 | Casper | A61N 5/0618 607/88 |

OTHER PUBLICATIONS

James et al. Controlled exposure to light and darkness realigns the salivary cortisol rhythm in night shift workers, Chronobiol Int., 2004, 961-72, 21(6).
Johns et al. Reliability and factor analysis of the Epworth Sleepiness Scale, Sleep, 1992, 376-81, 15(4).
Kaminski et al. Examining the stability of Automated Neuropsychological Assessment Metric (ANAM) baseline test scores, J Clin Exp Neuropsychol., 2009, 689-97, 31(6).
Kanno et al. Effects of zopiclone, flunitrazepam, triazolam and levomepromazine on the transient change in sleep-wake schedule: polygraphic study, and the evaluation of sleep and daytime condition, Prog Neuropsychopharmacol Biol Psychiatry, 1993, 229-39, 17(2).
Kayumov et al. Blocking low-wavelength light prevents nocturnal melatonin suppression with no adverse effect on performance during simulated shift work, J Clin Endocrinol Metab., 2005, 2755-61, 90(5).

(Continued)

*Primary Examiner* — Christine H Matthews
*Assistant Examiner* — Joshua D Lannu
(74) *Attorney, Agent, or Firm* — Kathleen D. Rigaut; Dann, Dorfman, Herrell and Skillman, P.C.

(57) ABSTRACT

A method and device for improving sleep performance of a subject exposed to an artificially lighted environment at night are provided, which involve selectively substantially blocking retinal exposure of the subject to light of specified wavelengths during the night.

27 Claims, 8 Drawing Sheets

(56) References Cited

OTHER PUBLICATIONS

Lamond et al. The impact of a week of simulated night work on sleep, circadian phase, and performance, Occup Environ Med., 2003, e13, 60(11).
Lee et al. A compromise phase position for permanent night shift workers: circadian phase after two night shifts with scheduled sleep and light/dark exposure, Chronobiol Int., 2006, 859-75, 23(4).
Lockley et al. Short-wavelength sensitivity for the direct effects of light on alertness, vigilance, and the waking electroencephalogram in humans, Sleep, 2006, 161-8, 29(2).
Ohayon et al. Consequences of shiftworking on sleep duration, sleepiness, and sleep attacks, Chronobiol Int., 2010, 575-89, 27(3).
Brainard et al. Action spectrum for melatonin regulation in humans: evidence for a novel circadian photoreceptor, J Neurosci., 2001, 6405-12, 21(16).
Cajochen et al. High sensitivity of human melatonin, alertness, thermoregulation, and heart rate to short wavelength light, J Clin Endocrinol Metab. 2005, 1311-6, 90(3).
Chellappa et al. Non-visual effects of light on melatonin, alertness and cognitive performance: can blue-enriched light keep us alert? PLoS One, 2011, e16429, 6(1).
Crowley et al. Combinations of bright light, scheduled dark, sunglasses, and melatonin to facilitate circadian entrainment to night shift work, J Biol Rhythms, 2003, 513-23, 18(6).
Czeisler et al. Exposure to bright light and darkness to treat physiologic maladaptation to night work, N Engl J Med. 1990, 1253-9, 322(18).
Czeisler et al. Modafinil for excessive sleepiness associated with shift-work sleep disorder, N Engl J Med. 2005, 476-86, 353(5).
Hemmeter et al. Effect of zopiclone and temazepam on sleep EEG parameters, psychomotor and memory functions in healthy elderly volunteers, Psychopharmacology (Berl). 2000, 384-96, 147(4).
Elsmore et al. The Ares® test system for palm OS handheld computers, Arch Clin Neuropsychol. 2007, S135-44, 22 Suppl 1.
Escriba et al. Shiftwork: its impact on the length and quality of sleep among nurses of the Valencian region in Spain, Int Arch Occup Environ Health. 1992, 125-9, 64(2).
Figueiro et al. Preliminary evidence that both blue and red light can induce alertness at night, BMC Neurosci. 2009, doi: 10.1186/1471-2202-10-105, 10:105.
Folkard et al. Modeling the impact of the components of long work hours on injuries and "accidents", Am J Ind Med. 2006, 953-63, 49(11).
Folkard et al. Do permanent night workers show circadian adjustment? A review based on the endogenous melatonin rhythm, Chronobiol Int. 2008, 215-24, 25(2).
Frese et al. Shiftwork and the length and quality of sleep, J Occup Med. 1984, 561-6, 26(8).
Gillooly et al. Circadian variation in human performance evaluated by the Walter Reed performance assessment battery, Chronobiology International, 1990, 143-153, 7(2).
Harrington et al. Health effects of shift work and extended hours of work, Occup Environ Med. 2001, 68-72, 58(1).
Horowitz et al. Efficacy of bright light and sleep/darkness scheduling in alleviating circadian maladaptation to night work, Am J Physiol Endocrinol Metab. 2001, E384-91, 281(2).
Kanno et al. Effects of zopiclone, flunitrazepam, triazolam and levomepromazine on the transient change in sleep-wake schedule: polygraphic study, and the evaluation of sleep and daytime condition, Prog Neuropsychopharmacol Biol Psychiatry. 1993, 229-39, 17(2).
Thorne et al. The Walter Reed performance assessment battery, Neurobehav Toxicol Teratol. 1985, 415-8, 7(4).
Smith et al. Evaluation of three circadian rhythm questionnaires with suggestions for an improved measure of morningness, J Appl Psychol. 1989, 728-38, 74(5).
Radloff et al. The CES-D Scale: A self report depression scale for research in the general population, Applied Psychological Measurement, 1977, 385-401, 1(3).
Rahman et al. Spectral modulation attenuates molecular, endocrine, and neurobehavioral disruption induced by nocturnal light exposure, Am J Physiol Endocrinol Metab. 2011, E518-27, 300(3).
Revell et al. Alerting effects of light are sensitive to very short wavelengths, Neurosci Lett. 2006, 96-100, 399(1-2).
Santhi et al. Scheduling of sleep/darkness affects the circadian phase of night shift workers, Neurosci Lett. 2005, 316-20, 384(3).
Santhi et al. Acute sleep deprivation and circadian misalignment associated with transition onto the first night of work impairs visual selective attention, PLoS One. 2007, e1233, 2(11).
Sasseville et al. Wearing blue-blockers in the morning could improve sleep of workers on a permanent night schedule: a pilot study, Chronobiol Int. 2009, 913-25, 26(5).
Smith et al. A compromise circadian phase position for permanent night work improves mood, fatigue, and performance, Sleep. 2009, 1481-9, 32(11).
Thapan et al. An action spectrum for melatonin suppression: evidence for a novel non-rod, non-cone photoreceptor system in humans, J Physiol. 2001, 261-7, 535(Pt 1).
Wessman et al. Assessing depressive symptoms in five psychiatric populations: a validation study, Am J Epidemiol. 1977, 203-14, 106(3).

\* cited by examiner

Fig. 3A
Fig. 3B
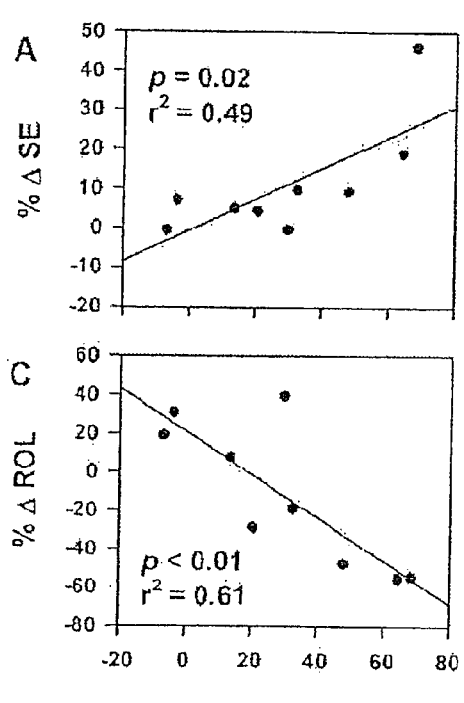
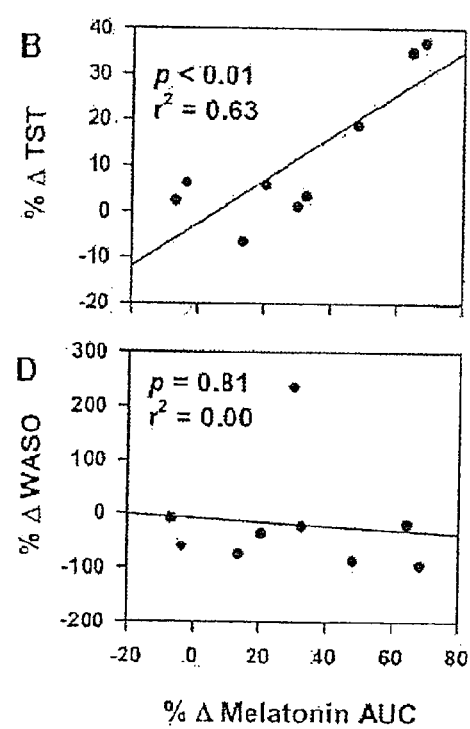
Fig. 3C
Fig. 3D

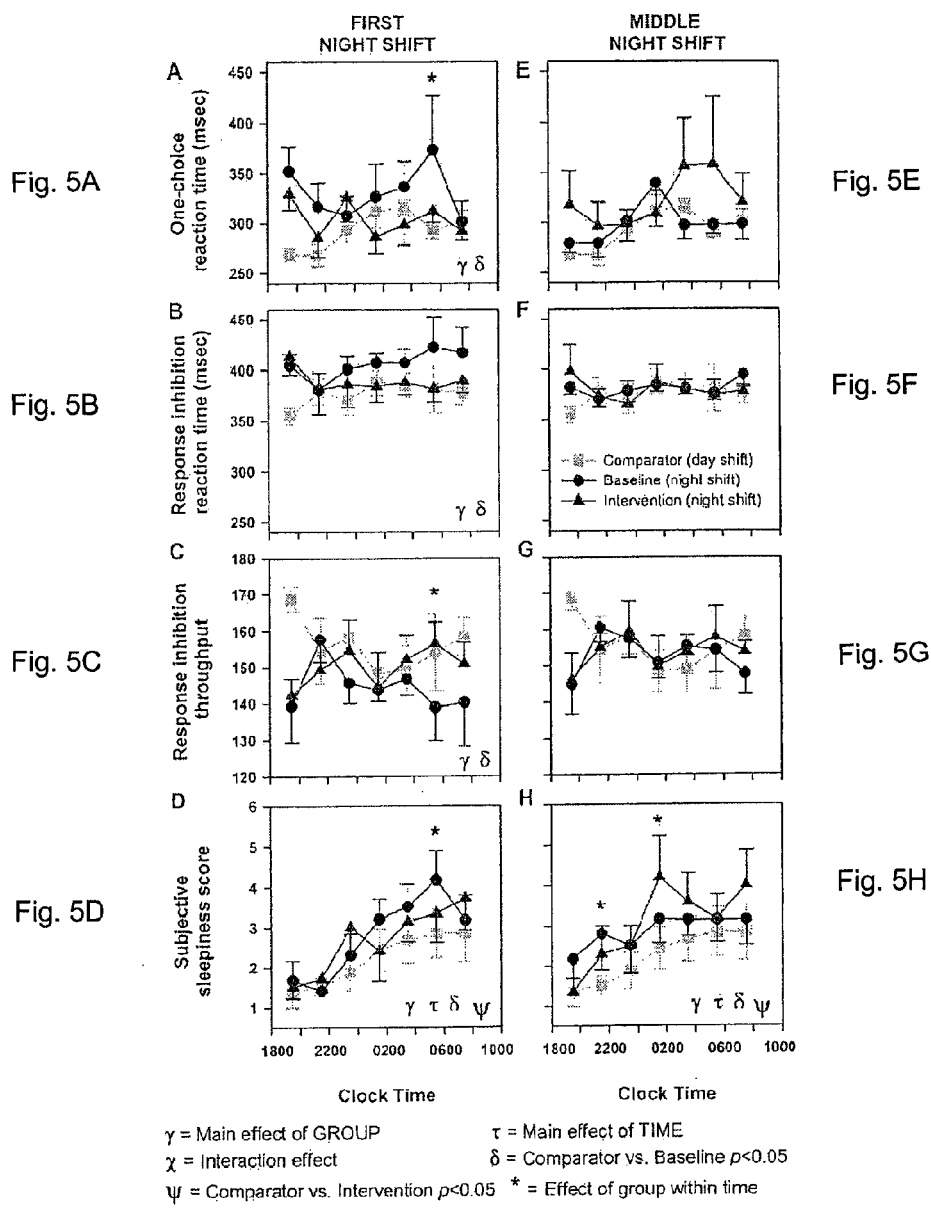

METHODS AND DEVICES FOR IMPROVING SLEEP PERFORMANCE IN SUBJECT EXPOSED TO LIGHT AT NIGHT

This application claims priority from U.S. Application No. 61/810,985 filed Apr. 11, 2013, the contents of which is incorporated by reference in its entirety.

FIELD OF THE INVENTION

The present invention relates to methods and devices for improving sleep performance in a subject exposed to light at night.

BACKGROUND OF THE INVENTION

Shift work forces individuals to be awake and perform at a time when biological sleep propensity is high and conversely to sleep when sleep propensity is minimal. This misalignment induces poor sleep and impaired alertness and performance. In addition, irregular light-dark cycles as a consequence of rotating between diurnal and nocturnal work schedules can induce circadian disruption (James et al., 2004; Santhi et al., 2005). Circadian and sleep disruption are linked to adverse health effects, and epidemiological studies have demonstrated a strong association between shift work and adverse health effects ranging from mood disorders to various forms of cancer (Harrington et al., 2001).

Different approaches have been tested for improving sleep and performance in shift workers. These include acute solutions such as the use of hypnotics to facilitate daytime sleep and/or the use of stimulants to improve performance during night work. Another approach involves inducing either partial (Lee et al., 2006; Smith et al., 2009) or complete (Czeisler et al., 1990; Horowitz et al., 2001; Santhi et al., 2005) circadian phase realignment such that the endogenous circadian phase for sleep and alertness correspond appropriately to external sleep and work schedules respectively. Since light is the strongest circadian resetting cue, a regimen of exposure to bright light during night work and darkness during scheduled daytime/evening sleep can be used to treat physiological maladaptation to night work. While complete inversions are the most effective in improving alertness, performance and sleep, they may be difficult to induce in a home-based setting and a complete inversion of circadian rhythms is seldom achieved, even across successive night shifts and after years of night work experience (Folkard et al., 2008). One of the practical difficulties with maintaining inverted circadian rhythms is exposure to bright light at times when individuals have to remain in darkness, for example exposure to sunlight during morning commutes or having to meet daytime social obligations (Crowley et al., 2003; Sasseville et al., 2009). In addition, it may be difficult to induce large (12-hour) phase shifts rapidly to completely invert rhythms when there is limited time between day and night shifts.

Recent work using simulated night shift paradigms suggest that a compromise circadian phase position, such that the highest circadian propensity for sleep occurs in the morning (~1000 h), may improve performance during night shifts and improve sleep during the daytime after night shifts and during the late-night on non-working days (Lee et al., 2006). In order to attain such a compromise phase position, individuals were exposed to four or five bright light (~4100 lux) pulses during their simulated night shifts, used dark sunglasses (15% average transmission; 0% below 400 nm) during daytime hours while they were awake, and had scheduled sleep episodes during the day (while on night shifts). This approach of achieving a compromise-phase position involves the use of dark sunglasses to minimize the resetting effects of light when an individual is awake but needs to remain in darkness to prevent unwanted circadian phase resetting.

An alternate approach exploits the differential sensitivity of the circadian pacemaker to short-wavelength light for photic phase resetting (Brainard et al., 2001; Thapan et al, 2001). Recent work has demonstrated that using glasses that attenuate short-wavelengths (less than 25% transmission <530 nm) during the morning and restrict light exposure at nighttime improved sleep in permanent night shift workers (Sasseville et al., 2009).

SUMMARY OF THE INVENTION

In one aspect, there is disclosed a method of improving sleep performance of a subject exposed to an artificially lighted environment at night comprising selectively substantially blocking retinal exposure of the subject to light of wavelengths less than about 490 nm during the night.

In another aspect, there is disclosed a method of improving sleep performance of a subject exposed to an artificially lighted environment at night comprising selectively substantially blocking retinal exposure of the subject to light of wavelengths less than about 480 nm during the night.

In another aspect, there is disclosed a method of improving sleep performance in a subject exposed to an artificially lighted environment at night comprising selectively substantially blocking retinal exposure of the subject to light of wavelengths selected from the group consisting of between about 410 nm and about 490 nm; between about 415 nm and about 490 nm between about 420 nm and about 490 nm; between about 425 nm and about 490 nm; between about 410 nm and about 480 nm; between about 415 nm and about 480 nm; between about 420 nm and about 480 nm; and between about 425 nm and about 480 nm; during the night.

In another aspect, there is disclosed a device for improving sleep performance of a subject exposed to light at night comprising an optical filter that selectively substantially blocks light of wavelengths selected from the group consisting of less than about 490 nm; less than about 480 nm; between about 410 nm and about 490 nm; between about 415 nm and about 490 nm between about 420 nm and about 490 nm; between about 425 nm and about 490 nm; between about 410 nm and about 480 nm; between about 415 nm and about 480 nm; between about 420 nm and about 480 nm; and between about 425 nm and about 480 nm; wherein the improved sleep performance comprises one or more of reduced sleep onset latency; an increase in total sleep time; a reduction in wake after sleep onset; an increase in rapid eye movement (REM) sleep; and a decrease in the time to onset of rapid eye movement (REM) sleep after sleep onset.

DESCRIPTION OF THE DRAWINGS

FIG. 2A shows the first night shift. FIG. 2B shows the middle night shift. FIG. 2C shows average melatonin profiles. FIG. 2D illustrates the 12-h area under the curve (AUC) for each individual compared between baseline and intervention conditions.

FIGS. 3A, 3B, 3C, and 3D show the correlation between percentage change in melatonin AUC between baseline and intervention conditions on the first night shift and the change in nighttime sleep structure variables [FIG. 3A: sleep efficiency (SE); FIG. 3B: total sleep time (TST); FIG. 3C: REM Onset Latency (ROL); FIG. 3D: wake after sleep onset (WASO).]

FIGS. 5A, 5B, 5C, 5D, 5E, 5F, 5G, and 5H show the effects of filtering short-wavelengths <480 nm from ambient light during night shifts on subjective and objective measures of alertness. FIG. 5A shows the effect on a one-choice reaction time on the first night shift. FIG. 5B shows the effect on response inhibition time on the first night shift. FIG. 5C shows the effect on response inhibition throughput on the first night shift. FIG. 5D shows the subjective sleepiness score on the first night shift. FIG. 5E shows the effect on a one-choice reaction time on the middle night shift. FIG. 5F shows the effect on response inhibition time on the middle night shift. FIG. 5G shows the effect on response inhibition throughput on the middle night shift. FIG. 5H shows the subjective sleepiness score on the middle night shift.

DETAILED DESCRIPTION OF THE INVENTION

Figure 1A:
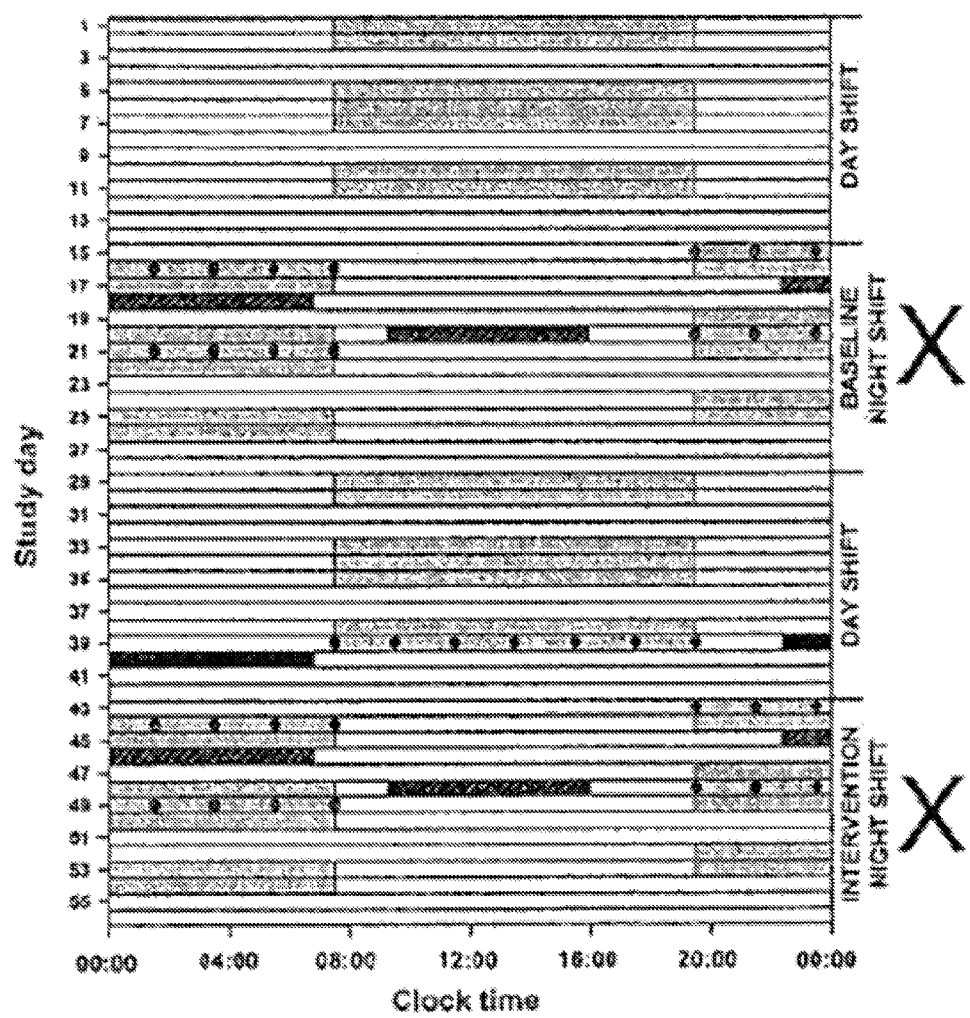
FIG. 1A shows a schematic representation of the study protocol of Example 1.

The present invention may be accomplished by various means. The following provides a definition for some of the terms used in the specification:

In the method of the present invention, the "subject" is a mammal, preferably a human.

"Substantially blocks" or "substantially blocking", when used in terms of wavelength of light, is defined as transmitting less than 20 percent of the incident wavelengths; less than 10 percent of the incident wavelengths; less than 5 percent of the incident wavelengths; and less than 1 percent of the incident wavelengths.

"Selectively blocking" refers to substantially blocking only those wavelengths of light specified, while allowing substantial transmission (i.e. transmission of more than 80 percent; of more than 90 percent; of more than 95 percent; or of more than 99 percent) of the other wavelengths of light in the subject's environment.

"About" in the context of wavelength ranges refers to +/− 5 nm.

In the context of the present invention, an "optical filter" is a device that substantially blocks (as this term is defined above) a range of non-transmitted wavelengths of light. As will be understood by a person of skill in the art, in this context, the term optical filter is not to be understood as equivalent to a colour filter, which, while transmitting light having a certain visual colour may not "substantially block" wavelengths of light outside those of the transmitted visual colour.

"Retinal exposure" refers to light impingement upon the retina of a subject.

"Night" refers to the natural hours of darkness and, more specifically, to the dark phase of the geophysical light/dark cycle. In summer, in peri-equatorial latitudes, this is roughly equivalent to about 2100 hrs (9 pm) to about 0600 hr (6 am). "During the night" refers to any time during this period; preferably, the method of the present invention is practiced throughout the night.

"Eyewear" is used as a broad term to encompass such items as eyeglasses, goggles, contact lenses and the like, that are used in connection with the eyes of a user to either shield/protect the eyes from harmful substances, for example chemicals in the context of goggles or to enhance the eyesight of the user, for example contact lenses. It will be understood that the term "eyewear" is not limited to the above examples, and describes any device used in connection with the eyes that contains a viewing window of sorts. Suitably, the eyewear of the present invention is designed to substantially prevent impingement of unfiltered light on the retina of the wearer.

"Improved sleep performance" means one or more of reduced sleep onset latency; an increase in total sleep time; a reduction is wake after sleep onset; an increase in rapid eye movement (REM) sleep; and a decrease in the time to onset of rapid eye movement (REM) sleep after sleep onset.

Light is the strongest environmental stimulus that resets circadian rhythms. Scheduled exposure to bright light during the night shift, and darkness during the day, improves circadian alignment to the inverted shift-work sleep and activity schedules and is associated with improved daytime sleep and nighttime performance. While this approach may be feasible in permanent shift workers, the short rotation times between shifts in rotating shift work does not allow sufficient time to induce adaptation to either night shifts or day shifts. Total sleep time may be reduced by up to 2-hours in shift workers as compared with non-shift workers (Escriba et al., 1992; Frese et al., 1984; Ohayon et al., 2010). Subjective reports of sleep disruption include sleep onset insomnia, premature awakenings, and poor sleep quality (Escriba et al., 1992; Frese et al., 1984). Both nighttime and daytime sleep may be adversely affected due to circadian misalignment induced by repeated rotations between night and day shifts.

The present inventors have unexpectedly found that light filtering intervention during the night shift significantly increases total sleep time and sleep efficiency during nocturnal sleep on non-working days immediately following two consecutive night shifts. These changes were primarily mediated by a reduction in sleep onset latency and wakefulness after sleep onset, evidencing a reduction in sleep initiation difficulty and sleep fragmentation and overall improvement in nocturnal sleep. Non-REM and REM sleep onset latency were also decreased following intervention.

While monochromatic blue (460 nm) light has previously been shown to improve alertness as compared with monochromatic green (555 nm) as demonstrated by faster reaction times and reduced lapses on psychomotor vigilance tests suggesting a short-wavelength dependency of cognitive performance (Cajochen et al., 2005; Chellappa et al., 2011; Lockley et al., 2006; Revell et al., 2006), the present inventors did not find a reduction in alertness levels, as would be expected from the results of previous monochromatic exposure studies, by removing the short-wavelengths such as ~460 nm and leaving mid-wavelengths such as ~555 nm (Kayumov et al., 2005; Rahman et al., 2011; Sasseville et al., 2009). Generally, studies reporting improvement in performance have used monochromatic light over an acute (≤6.5-h) exposure whereas in the current study, differences in performance were observed ~8 to 10-h after the onset of photic spectral modulation.

The present inventors did not observe adverse effects of filtering short-wavelengths on overall affect regulation during nocturnal shift work and did observe a significant improvement in subjective mood when assessed weekly following photic spectral modulation. Both circadian and sleep disruption are associated with mood impairment and are a common comorbidity in circadian rhythm sleep disorders and shift work.

As illustrated by the Examples below, photic spectral modulation during nocturnal work to remove short-wavelengths that induce maximal circadian phase resetting improves nocturnal sleep on non-working days without adversely affecting task performance. No differences were observed in one-choice reaction times following intervention as compared to baseline. Moreover, slower reaction times and increased throughput (accuracy) were observed on response inhibition and running memory tasks in the early morning, providing evidence of less impulsivity and better continuous task performance at the end of the night shift when most errors and accidents tend to occur.

Accordingly, in one embodiment, the invention is a method of improving the sleep performance of a subject exposed to an artificially lighted environment at night by selectively substantially blocking retinal exposure of the subject to light of wavelengths less than about 490 nm during the night. In another embodiment, the invention is a method of improving sleep performance of a subject exposed to an artificially lighted environment at night by selectively substantially blocking retinal exposure of the subject to light of less than about 480 nm during the night. Optimally, the method is practiced throughout the night.

In another embodiment, the invention is a method of improving sleep performance in a subject exposed to an artificially lighted environment at night by selectively substantially blocking retinal exposure of the subject to light of wavelengths between about 410 nm and about 490 nm; between about 415 nm and about 490 nm between about 420 nm and about 490 nm; between about 425 nm and about 490 nm; between about 410 nm and about 480 nm; between about 415 nm and about 480 nm; between about 420 nm and about 480 nm; and between about 425 nm and about 480 nm; during the night. Optimally, the method is employed throughout the night.

In one embodiment, the invention is a device for improving sleep performance in a subject exposed to an artificially lighted environment at night. The device includes an optical filter for selectively substantially blocking light of wavelengths less than about 490 nm; and light of wavelengths less than about 480 nm.

In another embodiment, the invention is a device for improving the sleep performance of a subject exposed to an artificially lighted environment at night that includes an optical filter for selectively blocking light of wavelengths between about 410 nm and about 490 nm; between about 415 nm and about 490 nm; between about 420 nm and about 490 nm; between about 425 nm and about 490 nm; between about 410 nm and about 480 nm; between about 415 nm and about 480 nm; between about 420 nm and about 480 nm; and between about 425 nm and about 480 nm; during the night. These optical filters enable good colour recognition and do not impart a significant yellow hue. They also permit an average user to distinguish between most shades of white/grey/yellow and blue/green/black.

In another embodiment of the invention, an optical filter such as those described above may be applied to the surface of a light source, including an incandescent or fluorescent light bulb. In one embodiment, the optical filter is in the form of a coating.

In another embodiment, a transparent or semi-transparent cover including an optical filter as described above can be releasably attached to a light source to channel the light emitted from the light source through the cover. A light source can include devices that emit light, although this is not their primary function, for example a television screen or a computer monitor. It will be understood by a person skilled in the art that the cover may be any shape or form as long as it is operable to cover the light source that it is to be used with. In an alternative embodiment, the light cover can be permanently attached to a light source.

In another embodiment, the invention is a light source for improving the sleep performance of a subject exposed to an artificially lighted environment at night that excludes wavelengths of light less than about 490 nm; less than about 480 nm; between about 410 nm and about 490 nm; between about 415 nm and about 490 nm; between about 420 nm and about 490 nm; between about 425 nm and about 490 nm; between about 410 nm and about 480 nm; between about 415 nm and about 480 nm; between about 420 nm and about 480 nm; and between about 425 nm and about 480 nm. In one embodiment, the light source is a display screen.

In another embodiment, the invention is eyewear for improving the sleep performance of a subject exposed to an artificially lighted environment at night that includes an optical filter for blocking light of wavelengths less than about 490 nm; less than about 480 nm; between about 410 nm and about 490 nm; between about 415 nm and about 490 nm between about 420 nm and about 490 nm; between about 425 nm and about 490 nm; between about 410 nm and about 480 nm; between about 415 nm and about 480 nm; between about 420 nm and about 480 nm; and between about 425 nm and about 480 nm. In one embodiment, the optical filter is in the form of a coating.

EXAMPLES

The effects of selectively filtering short-wavelengths <480 nm, only during night shifts, on nighttime sleep when individuals maintained a daytime activity schedule and daytime sleep when individuals maintained a nighttime activity schedule and the effects of photic spectral modulation on affect and cognitive performance were examined.

Thirty-six fulltime nurses working rotating shifts at the same hospital were interviewed for the study and fourteen were included as meeting the selection criteria for the study. The results from nine participants with the same shift are presented. The participants included 5 females and 4 males; mean age (±SD): 31.3±4.6 years. Participants were screened for extreme chronotype as assessed with the composite scale of morningness (Smith et al., 1989) (exclusion range: <22 and >44; mean±SD: 34.2±4.3; 29-43); history of ocular/vision diseases including requirement of corrective lenses for vision and/or color blindness; depressive symptomatology based on the Centre for Epidemiologic Studies Depression Scale (CES-D) score (Weissman et al., 1977) (exclusion >16; mean±SD: 8.4±3.3; 2-14); any medication use; occasional or habitual nicotine use. None of the participants worked elsewhere or on other shifts within the department besides the study schedule while enrolled in the study. Participants were recruited from Emergency, Medical/Surgical/Neurological intensive care unit, and the Musculoskeletal Health and Arthritis units.

Each participant was enrolled in the study for eight-weeks. Twelve hour night (1930 to 0730 h) and day (0730 to 1930) shifts were worked in two-week stretches with no more than two or three consecutive work-days and no less than two consecutive work-days (FIG. 1A). Participants did not rotate between night and day shifts during the two-week stretch, that is, the subjects completed two weeks of night shifts alternating with 2 weeks of day shifts. All work shifts were separated by two to three non-working days during both night and day shift stretches. All subjects started the study with two-weeks of day shifts. Subjects were then randomized to receive glasses fitted with short-wavelength filters (0% transmission <480 nm) (FIG. 1B) to be used only during night shifts during Weeks 3 and 4 (Days 15-28) or 7 and 8 (Day 43-56). Subjects were not allowed to consume stimulants including caffeine on any of the testing nights and prior to nighttime and daytime sleep studies; however, caffeine use was allowed on other days. Participants were not allowed to nap during work.

Nighttime and daytime sleep was assessed in the sleep lab by polysomnography (PSG) on five separate occasions. Nighttime sleep was assessed after the first two night shifts with (intervention) and without (baseline) short-wavelength filtering glasses. The first exposure to the sleep lab was randomized between baseline (5 subjects) and intervention (4 subjects) to control for any acclimatization and first-night effects. In addition, nighttime sleep was assessed on the last day shift of the second two-week stretch of day shifts (comparator) (FIG. 1A). Daytime sleep was assessed between the third and fourth night shifts with (intervention) and without (baseline) short-wavelength filtering glasses. Saliva samples were collected for melatonin assays every 2-h during the first night shift and during the middle night of three night shifts under baseline and intervention conditions (FIG. 1A). Subjective and objective assessment of alertness was conducted on the first and middle night shift under baseline and intervention conditions as well as on the last day shift of the second two-week stretch of day shifts (FIG. 1A).

While working, participants were exposed to a mean light intensity of 179.4±48.3 lux (mean±SD) generated mostly from overhead fluorescent lamps. The range of lowest to highest intensities for the different hospital units where the nurses in the study worked was 41.3 to 480.4 lux. Exposure to light during working or non-working hours was not controlled but individuals were instructed to maintain consistent daytime and nighttime sleep-wake schedules throughout the study.

Figure 1B:
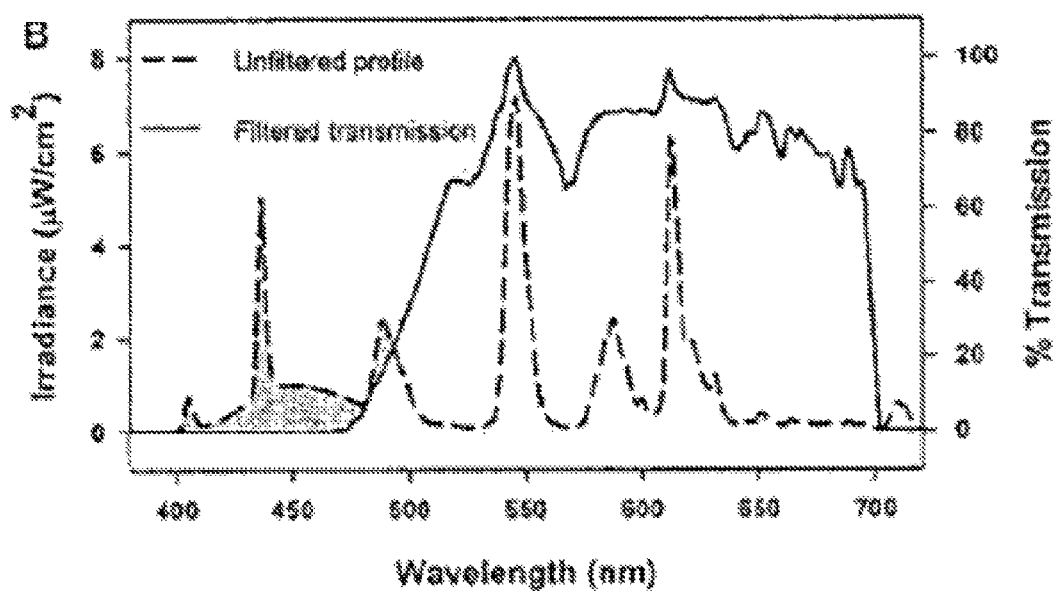
FIG. 1B shows spectral transmission of filtered light in Example 1.

The filters used in the study for photic spectral modulation have been characterized and described in detail elsewhere (Rahman et al., 2011). Visual short-wavelengths were filtered from ambient light during night shifts using identical wrap-around spectacle frames fitted with polycarbonate lenses coated with thin-film Fabry-Perot interference filters that blocked all transmission (0% transmission) below 480 nm (ZircLight Inc., Stoneham, Mass., USA; FIG. 1B). The direct application of the thin-film filters onto the lenses and the use of wrap-around frames ensured a single unit filtering device minimizing stray light incident on the eyes. The spectral transmission profile generated using a common fluorescent light source (T-8 48" 32 Watt—F032/850 5000K Octron Eco Fluorescent Bulb; Osram Sylvania, Ontario, Canada) is presented in FIG. 1B. The 1931 CIE x/y chromaticity values for the filtered lenses derived from a fluorescent source was 0.487/0.500 respectively (Rahman et al., 2011).

Example 1

Endocrine Measures

Melatonin and cortisol were assayed in saliva. The results reported for cortisol assays include all fourteen individuals (9 females and 5 males) mean age (±SD): 28.3±4.7 years who met the selection criteria of the study. Eating or drinking was not permitted for 30 minutes prior to sample collection. Saliva was collected every 2-h and stored at 4° C. until all samples were collected at the end of the shift for each individual. All samples were stored in −80° C. until further processing. Two aliquots of each saliva sample were frozen separately for melatonin and cortisol assays, respectively, to minimize repeated freeze-thaw cycles. All frozen saliva samples were defrosted on ice and centrifuged again at 1,500×g for 15 min at 4° C. prior to assaying. Salivary melatonin and cortisol were measured by enzyme linked immunosorbent assays (Alpco Diagnostics, New Hampshire, USA and Cayman Chemical, Michigan, USA, respectively) as per manufacturer's instructions and as described in Rahman et al., 2011. All samples from each subject under each lighting condition were assayed in batches so that an equal number of samples from each of the two lighting conditions and subjects were processed together in each run of the assay. The intra-assay precisions were 2.1% at 1.5 pg/ml and 3.3% at 50 pg/ml and the inter-assay precisions were 2.9% at 1.5 pg/ml and 11.7% at 50 pg/ml and the limit of detection was 0.5 pg/ml. For the cortisol assay, the intra-assay variation was 1.1% at 4000 pg/ml and 13.4% at 41.0 pg/ml and the inter-assay variation was 6.7% at 4000 pg/ml and 25.8% at 41.0 pg/ml. The limit of detection was 6.6 pg/ml.

Effects on Melatonin and Cortisol Levels During Night Shifts

Figures 2A, 2B, 2C:
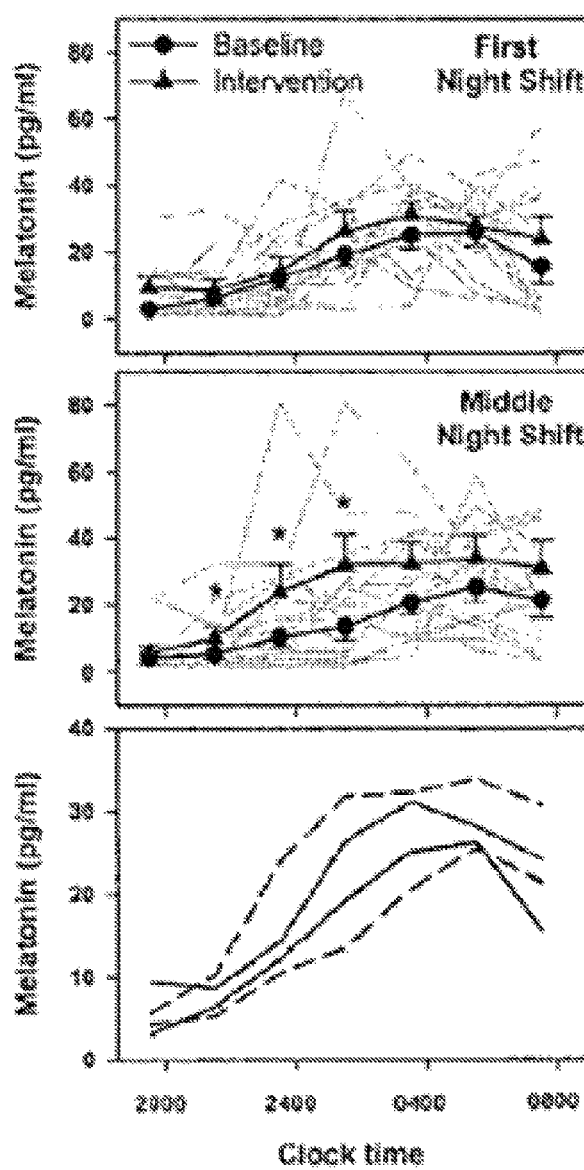
FIGS. 2A, 2B, 2C, and 2D show changes in melatonin levels during night shifts with exposure to visual short-wavelength filtered light and standard ambient artificial light.
Figure 2D:
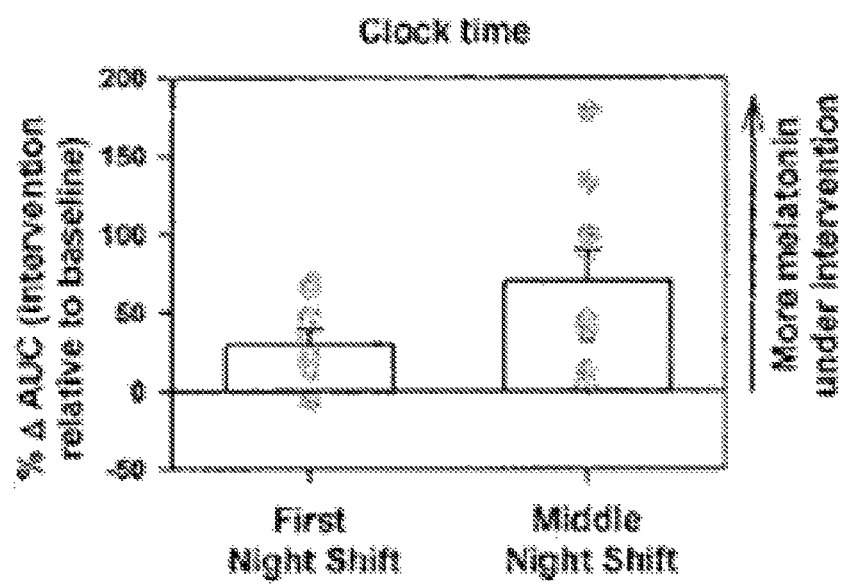

As compared to baseline, there was a modest but significant increase in melatonin levels with intervention (group effect p=0.04) (FIG. 2A) on the first night shift and a more robust difference on the middle night shift (p<0.01) (FIG. 2B). There was a significant effect of time on melatonin profiles on both nights (p<0.01) but no interaction-effects of the two factors (first night: p=0.95; fourth night: p=0.69). There was considerable inter-individual variation in absolute levels and peak-time on the first and middle night shifts and under both baseline and intervention conditions. The average melatonin profiles suggest a greater difference in phase on the middle night shift between baseline and intervention than on the first night shift (FIG. 2C). In addition, the 12-h area under the curve (AUC) for each individual compared between baseline and intervention conditions revealed significantly greater change in melatonin AUC on the middle night as compared to first night shift (p=0.02) (FIG. 2D). Moreover, the change in melatonin AUC was more variable on the middle night shift (range: 3.7 to 178.1; SD: 58.2) as compared to the first night shift (range: −6.8 to 68.3; SD: 27.0) (FIG. 2D). There were significant correlations on the first night shift between changes in melatonin AUC and the changes in sleep efficiency (p=0.02; FIG. 3A) and total sleep time (p<0.01; FIG. 3B) for nighttime sleep but not daytime sleep (FIGS. 3C and D).

Figure 4:
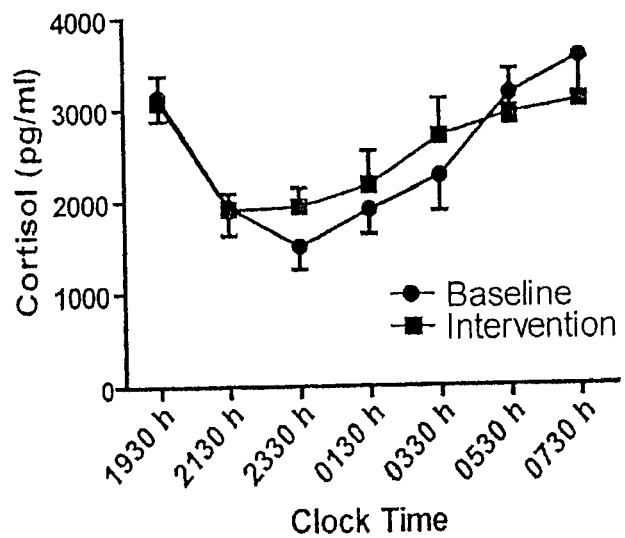
FIG. 4 shows salivary cortisol levels during night shifts with exposure to visual short-wavelength filtered light and standard ambient artificial light.

As compared to baseline, intervention did not affect cortisol levels during the night shift. As shown in FIG. 4, there was a significant effect of time (F(6,164)=7.310, p<0.001) but not of spectral modulation or the interaction of both on cortisol levels. Statistically significant values at specific times as revealed by post hoc analysis are represented by * for p<0.01.

Example 2

Polysomnographic Sleep Assessment

All individuals arrived at the sleep laboratory for nocturnal sleep studies at 2030 h and had a mandatory lights-off no later than 2400 h. This approach ensured a minimum 8-h sleep opportunity and wake-up within 1-h of habitual shift start time if the individuals were to return to day shift the following morning. For daytime sleep all individuals arrived at the sleep laboratory at 0800 h and had a mandatory lights-off no later than 1000 h. This ensured a minimum 8-h sleep opportunity before the individuals had to return to their next night shift the same evening at 1900 h. Individuals could choose to turn lights off and initiate sleep earlier than the mandatory lights-off time but not later than the pre-set time.

Individuals were allowed to sleep longer than 8-h. If an individual awoke prior to 8-h being completed in any sleep episode they were kept in bed for an additional hour with the lights-off before the sleep episode was terminated. This was to ensure that individuals did not forcibly truncate their sleep. In addition, participants slept in private rooms with no access to electronics including alarm clocks, cellular phones or other devices with time-telling capability or illuminated screens. The extra hour was not added to the total sleep time or time in bed if the participants did not sleep (have stage two or higher or REM sleep) during that period; however, if subjects did sleep for any portion within that 1-h period that duration was added to total sleep time and any intervening wake was added to wake after sleep onset.

Sleep was assessed objectively using polysomnography (PSG) and data were collected and analyzed using the Sandman Elite system (Kanata, Ontario, Canada). A standard montage including electroencephalography, electrooculography, electromyography and respiratory monitoring (oxygen saturation, nasal airflow, and breathing effort) was used. The polysomnography were scored by a single blinded scorer according to standardized criteria (Rechtschaffen & Kales, 1968). The sleep parameters included sleep onset latency (SOL); total sleep time (TST); sleep efficiency % (SE; percentage of total sleep time to total time in bed); wakefulness after sleep onset (WASO); duration of each NREM sleep stage; duration of REM sleep; REM latency; absolute number of arousals in the total sleep episode and absolute number of stage shifts. SOL was defined as time to the first thirty-second epoch of stage 2 sleep from lights-off.

Effects on Nighttime and Daytime Sleep

The main effects of group and significance levels are presented in Table 1 for nighttime sleep and Table 2 for daytime sleep. Nighttime sleep assessed under baseline and intervention conditions following two night shifts was compared to nighttime sleep after two weeks of day shifts (comparator). Mean lights-off and lights-on time were not significantly different between the three conditions. There were significant reductions in total sleep time, sleep efficiency, NREM (Stage 2+3+4) duration and a significant increase in wake after sleep onset (WASO) under baseline as compared to comparator. The use of optical filters (intervention) improved all of these parameters so that they were no longer significantly different from the comparator. Total sleep time was increased by a mean of 40 minutes after intervention compared to baseline. WASO was reduced by a mean of 22 minutes and sleep onset latency was reduced by a mean of about 8 minutes during the night following intervention compared to baseline. There was no change in slow wave sleep with intervention or baseline compared to the comparator night.

Daytime sleep assessed under baseline and intervention conditions between two night shifts was also compared to the comparator, i.e. the same nighttime sleep episode after two weeks of day shifts was used for both day sleep and night sleep comparisons. There was a significant increase in WASO during day sleep under baseline compared to the comparator. Under intervention, WASO was not different from the comparator night sleep. There were significant reductions in total sleep time, sleep efficiency, stage 2 duration, REM and NREM (Stage 2+3+4) duration under baseline during day sleep compared to the comparator (Table 2). Under intervention, all day sleep parameters were improved toward the comparator values.

TABLE 1

Effects of filtering visual short-wavelengths <480 nm on nighttime sleep structure variables.

| | COMPARATOR (C) Mean ± SEM | BASELINE (B) Mean ± SEM | INTERVENTION (I) Mean ± SEM | p | C vs. B | C vs. I |
|---|---|---|---|---|---|---|
| Total sleep time (min) | 476.67 ± 17.32 | 397.67 ± 18.67 | 437.78 ± 14.37 | 0.0107 | 0.0067 | 0.2375 |
| Sleep efficiency (%) | 91.42 ± 1.40 | 78.14 ± 4.01 | 85.94 ± 3.32 | 0.0221 | 0.0142 | 0.5763 |
| Stage 1 (min) | 29.00 ± 7.97 | 22.67 ± 3.92 | 20.39 ± 2.50 | 0.5416 | | |
| Stage 2 (min) | 231.80 ± 9.87 | 217.28 ± 15.17 | 238.56 ± 7.53 | 0.2371 | | |
| Stage 3 (min) | 18.58 ± 1.42 | 19.83 ± 2.53 | 22.06 ± 2.60 | 0.6210 | | |
| Stage 4 (min) | 77.83 ± 10.37 | 51.83 ± 5.11 | 63.31 ± 9.97 | 0.1667 | | |
| REM (min) | 120.17 ± 13.10 | 85.50 ± 9.17 | 92.67 ± 9.73 | 0.1168 | | |
| NREM (S2 + S3 + S4) (min) | 327.50 ± 12.64 | 288.94 ± 17.00 | 323.92 ± 12.09 | 0.0476 | 0.0771 | 0.9973 |
| SWS (S3 + S4) (min) | 96.42 ± 9.71 | 71.67 ± 5.46 | 85.37 ± 10.57 | 0.1982 | | |
| Sleep onset latency (min) | 13.27 ± 5.76 | 14.37 ± 2.33 | 10.59 ± 1.89 | 0.6643 | | |
| REM onset latency (min) | 59.25 ± 11.21 | 103.28 ± 20.78 | 72.00 ± 4.05 | 0.0907 | | |
| WASO (min) | 22.42 ± 5.80 | 73.00 ± 21.43 | 37.39 ± 17.64 | 0.0237 | 0.0338 | 0.9147 |

TABLE 2

Effects of filtering visual short-wavelengths <480 nm on daytime sleep structure variables.

| | COMPARATOR (C) Mean ± SEM | BASELINE (B) Mean ± SEM | INTERVENTION (I) Mean ± SEM | p | C vs. B | C vs. I |
|---|---|---|---|---|---|---|
| Total sleep time (min) | 476.67 ± 17.32 | 307.78 ± 33.16 | 341.52 ± 25.86 | 0.0006 | 0.0004 | 0.0025 |
| Sleep efficiency (%) | 91.42 ± 1.40 | 68.32 ± 7.07 | 75.36 ± 3.99 | 0.0098 | 0.0053 | 0.0414 |
| Stage 1 (min) | 29.00 ± 7.97 | 20.22 ± 2.74 | 24.09 ± 3.13 | 0.4280 | | |
| Stage 2 (min) | 231.08 ± 9.87 | 147.22 ± 17.60 | 155.94 ± 10.59 | 0.0026 | 0.0021 | 0.0047 |
| Stage 3 (min) | 18.58 ± 1.42 | 17.00 ± 2.76 | 13.94 ± 1.74 | 0.4702 | | |
| Stage 4 (min) | 77.83 ± 10.37 | 64.33 ± 9.75 | 75.72 ± 9.32 | 0.2980 | | |
| REM (min) | 120.17 ± 13.10 | 58.50 ± 11.86 | 71.22 ± 11.67 | 0.0025 | 0.0014 | 0.0083 |
| NREM (S2+ S3 + S4) (min) | 327.50 ± 12.64 | 228.56 ± 22.05 | 245.61 ± 16.46 | 0.0026 | 0.0016 | 0.0068 |
| SWS (S3 + FS4) (min) | 96.42 ± 9.71 | 81.33 ± 10.11 | 89.67 ± 10.07 | 0.4624 | | |
| Sleep onset latency (min) | 13.27 ± 5.76 | 13.24 ± 4.16 | 4.76 ± 2.06 | 0.0673 | | |
| REM onset latency (min) | 59.25 ± 11.21 | 74.72 ± 9.90 | 76.89 ± 13.71 | 0.4565 | | |
| WASO (min) | 22.42 ± 5.80 | 88.72 ± 32.24 | 66.67 ± 22.10 | 0.0460 | 0.0269 | 0.1124 |

For Tables 1 and 2, data represent mean±SEM. Data were subjected to repeated measures one-factor (Group) mixed model ANOVA. If a significant main effect was observed the analysis was followed by Dunnett's multiple comparison tests to assess differences between intervention and baseline groups relative to the comparator group.

As described above, total sleep time after intervention was increased by a mean of 40 minutes compared to baseline after night shifts without using optical filters. To put these results into perspective, total sleep time has been shown to be increased by about 40 minutes in healthy elderly subjects taking the potent hypnotic, zopiclone 7.5 mg (Hemmeter et al., 2000), and by 40 to 70 minutes after zopiclone 10 mg in young healthy subjects on delayed or advanced sleep schedules, respectively (Kanno et al., 1993). Subjects in the present study also fell asleep faster and woke up less frequently after sleep onset, resulting in an improvement in sleep efficiency.

The present study demonstrates that filtering visual short-wavelengths during nocturnal work improves sleep duration and efficiency after consecutive night shifts.

Example 3

Neurobehavioral Measures

Participants completed self-report scales and objective tests programmed onto a hand held personal digital assistant (PDA). Each participant was given a unique PDA and all tests on the PDA were commercially programmed and validated (Behavioral Neuroscience System, LLC, Springfield, Mo., USA) (Elsmore et al., 2007). These tests are programmed on the PDA as part of the Automated Readiness Evaluation System (ARES) (Elsmore et al., 2007) which is an extension of the Automated Neuropsychological Assessment Metric (ANAM) (Kaminski et al., 2009), the latter being a computerized version of the Walter Reed Performance Assessment Battery (PAB) (Thorne et al., 1985).

The ARES battery allows selection of PAB tests to design a customized battery allowing reduction of total testing duration. Performance tests as part of the modified ARES battery included measures of one-choice reaction and response inhibition (GO/NO-GO) tests and subjective sleepiness was assessed using a 7-item self-report scale (Elsmore et al., 2007; Thorne et al., 1985). This battery has been shown to be sensitive to circadian variation (Gillooly et al., 1990) and has been used previously to study the effects of different visual wavelengths on cognitive performance (Figueiro et al., 2009). The one-choice reaction test required the participant to tap on an assigned spot on the PDA screen when presented with a single stimulus (an asterisk *) as fast as possible. The response inhibition test presented two non-simultaneous stimuli, where one required a screen-tapping response the other did not. The test durations were 1-min and 2-min for the one-choice reaction test and the response inhibition test respectively. At the end of each week, depressive symptomatology was assessed using the Center for epidemiologic studies depression scale (CES-D) (Radloff 1977) and subjective daytime sleepiness was assessed using the Epworth sleepiness scale (ESS) (Johns 1992).

On the first night shift there was a significant effect of group on one-choice reaction time ($p<0.01$), response inhibition task reaction time ($p=0.03$), response inhibition throughput ($p<0.01$) and subjective sleepiness ($p<0.01$) (FIG. 5A-D). There was a significant main effect of time only on subjective sleepiness ($p<0.01$). There was no significant effect of the interaction of the two factors on any of the cognitive parameters.

Reaction times under baseline night shifts were significantly slower as compared to daytime performance ($p<0.01$) whereas during intervention, reaction times were the same as during the daytime comparator ($p=0.55$) (FIG. 5A). Similarly, reaction time on the response inhibition task was significantly slower under baseline ($p=0.02$) but under intervention was similar ($p=0.44$) to daytime performance (FIG. 5B). In addition, throughput on the response inhibition test was significantly reduced under baseline ($p<0.01$) but maintained under intervention ($p=0.24$) compared to daytime performance (FIG. 5C). In contrast to objective performance, subjective sleepiness significantly increased over the course of the night shift under both baseline ($p<0.01$) and intervention ($p=0.01$) as compared to daytime sleepiness levels (FIG. 5D).

On the middle night shift of the run of three night shifts, there was a significant effect of group on subjective sleepiness ($p<0.01$) but not on any of the objective alertness measures (FIG. 5E-F). There was a significant main effect of time only on subjective sleepiness (p<0.01). There was no significant effect of the interaction of the two factors on any of the cognitive parameters. Similar to the first night shift, subjective sleepiness during the middle night shift was also significantly greater under baseline (p<0.01) and intervention (p<0.01) as compared to daytime sleepiness levels (FIG. 5D).

Figures 6A, 6B:
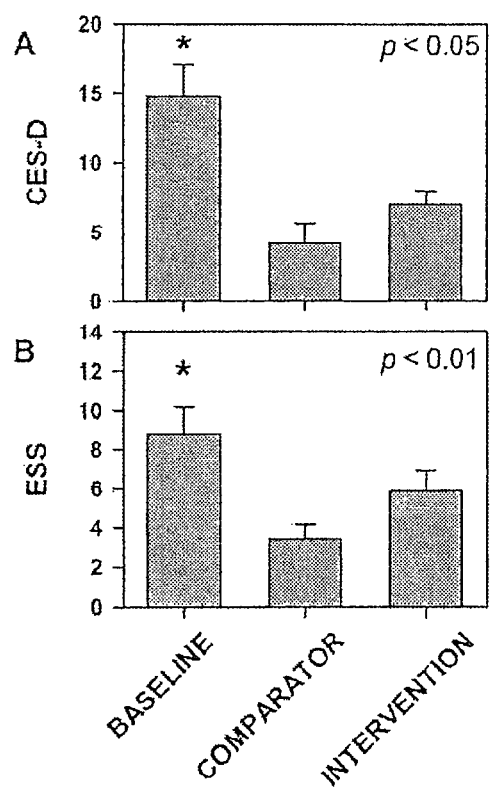
FIG. 6A shows the effect of filtering short wavelengths <480 nm from ambient light during night shifts on subjective mood.
FIG. 6B shows the effect of filtering short wavelengths <480 nm from ambient light during night shifts on daytime sleepiness.

After the first week of night shifts without intervention (baseline), subjective mood was significantly worse (FIG. 6A) and daytime sleepiness (FIG. 6B) was significantly higher as compared to comparator (day shift), whereas under intervention condition mood and daytime sleepiness were not different.

Filtering short wavelengths was not associated with reduced cognitive performance during the night shift as compared to the day shift. In contrast, under baseline conditions during the night shift there was a significant increase in reaction time and reduction in throughput as compared to daytime performance. An improvement in cognitive performance with intervention compared to baseline was observed toward the end of the night shift. A placebo effect is unlikely since subjective sleepiness was significantly increased under both intervention and baseline conditions contrary to cognitive performance. The observed improvement in cognitive performance with the optical filters would reduce the incidence of accidents and errors associated with increased fatigue at the end of shift.

The middle night shift of a run of three night shifts revealed no differences in cognitive performance between the baseline condition and day shift performance although subjective sleepiness was significantly higher. This suggests that there may have been some level of adaptation after several night shifts. This suggestion is in agreement with previous reports showing that cognitive performance impairment is greatest on the first night shift and gradually improves in successive shifts (Lamond et al., 2003; Santhi et al., 2007) although some reports have suggested otherwise (Folkard & Lombardi 2006).

While this invention has been described with reference to illustrative embodiments and examples, the description is not intended to be construed in a limiting sense. Thus, various modifications will be apparent to persons skilled in the art upon reference to this description.

Further, elements illustrated or described in connection with one exemplary embodiment may be combined with the features of other embodiments. Such modifications and variations are intended to be included within the scope of the present invention.

All publications, patents and patent applications referred to herein are incorporated by reference in their entirety to the same extent as if each individual publication, patent or patent application was specifically and individually indicated to be incorporated by reference in its entirety.

REFERENCES

Brainard G C, Hanifin J P, Greeson J M, Byrne B, Glickman G, Gerner E and Rollag M D. Action spectrum for melatonin regulation in humans: Evidence for a novel circadian photoreceptor. J Neurosci 21(16): 6405-6412, 2001.

Cajochen C, Munch M, Kobialka S, Krauchi K, Steiner R, Oelhafen P, Orgul S and Wirz-Justice A. High sensitivity of human melatonin, alertness, thermoregulation, and heart rate to short wavelength light. J Clin Endocrinol Metab 90: 1311-1316, 2005.

Chellappa S L, Steiner R, Blattner P, Oelhafen P, Gotz T and Cajochen C. Non-visual effects of light on melatonin, alertness and cognitive performance: can blue-enriched light keep us alert? PLoS ONE 6: e16429, 2011.

Crowley S J, Lee C, Tseng C Y, Fogg L F and Eastman C I. Combinations of bright light, scheduled dark, sunglasses, and melatonin to facilitate circadian entertainment to night shift work. J Biol Rhythms 18: 513-523, 2003.

Czeisler C A, Johnson M P, Duffy J F, Brown E N, Ronda J M and Kronauer R E. Exposure to bright light and darkness to treat physiologic maladaptation to night work. N Engl J Med 322: 1253-1259, 1990.

Czeisler C A, Walsh J K, Roth T, Hughes R J, Wright Jr. K P, Kingsbury L, Arora S, Schwartz J R L, Niebler G E and Dinges D F. Modafinil for excessive sleepiness associated with shift work sleep disorder. N Engl J Med 353: 476-486, 2005.

Elsmore T F, Reeves D L and Reeves A N. The ARES test system for palm OS handheld computers. Arch Clin Neuropsychol 22 Suppl 1: S135-S144, 2007.

Escriba V, Perez-Hoyos S and Bolumar F. Shiftwork: its impact on the length and quality of sleep among nurses of the Valencian region in Spain. Int Arch Occup Environ Health 64: 125-129, 1992.

Figueiro M G, Bierman A, Plitnick B, Rea M S. Preliminary evidence that both blue and red light can induce alertness at night. BMC Neurosci 10:105, 2009.

Folkard S. Do permanent night workers show circadian adjustment? A review based on the endogenous melatonin rhythm. Chronobiol Int 25: 215-224, 2008.

Folkard S, Lombardi D A. Modeling the impact of the components of long work hours on injuries and "accidents". Am. J Ind. Med., 2006.

Frese M and Harwich C. Shiftwork and the length and quality of sleep. J Occup Med 26: 561-566, 1984.

Gillooly P B, Smolensky M H, Albright D L, Hsi B, Thorne D R. Circadian variation in human performance evaluated by the Walter Reed performance assessment battery. Chronobiol Int 7:143-153, 1990.

Harrington, J. M. Health effects on shiftwork and extended hours of work. Occupational and Environmental Medicine 58, 68-72. 2001.

Hemmeter U, Muller M, Bischof R, Annen B, Holsboer-Trachsler E. Effect of zopiclone and temazepam on sleep EEG parameters, psychomotor and memory functions in healthy elderly volunteers. Psychopharmacology (Berl) 147: 384-396, 2000.

Horowitz T S, Cade B E, Wolfe J M and Czeisler C A. Efficacy of bright light and sleep/darkness scheduling in alleviating circadian maladaptation to night work. Am J Physiol Endocrinol Metab 281: E384-E391, 2001.

James F O, Walker C D and Boivin D B. Controlled exposure to light and darkness realigns the salivary cortisol rhythm in night shift workers. Chronobiol Int 21: 961-972, 2004.

Johns M W. Reliability and factor analysis of the Epworth sleepiness Scale. Sleep 15:376-381, 1992.

Kaminski T W, Groff R M and Glutting J J. Examining the stability of Automated Neuropsychological Assessment Metric (ANAM) baseline test scores. J Clin Exp Neuropsychol 31: 689-697, 2009.

Kanno O, Watanabe H, Kazamatsuri H. Effects of zopiclone, flunitrazepam, triazolam and levomepromazine on the transient change in sleep-wake schedule: polygraphic study, and the evaluation of sleep and daytime condition. Prog Neuropsychopharmacol Biol Psychiatry 17:229-239, 1993.

Kayumov L, Casper R F, Hawa R J, Perelman B, Chung S A, Sokalsky S and Shapiro C M. Blocking low-wavelength light prevents nocturnal melatonin suppression with no adverse effect on performance during simulated shift work. J Clin Endocrinol Metab 90: 2755-2761, 2005.

Lamond N, Dorrian J, Roach G D, McCulloch K, Holmes A L, Burgess H J, Fletcher A, Dawson D. The impact of a week of simulated night work on sleep, circadian phase, and performance. Occup. Environ. Med 60:e13, 2003.

Lee C, Smith M R and Eastman C I. A compromise phase position for permanent night shift workers: circadian phase after two night shifts with scheduled sleep and light/dark exposure. Chronobiol Int 23: 859-875, 2006.

Lockley S W, Evans E E, Scheer F A J L, Brainard G C, Czeisler C A and Aeschbach D. Short-wavelength sensitivity for the direct effects of light on alertness, vigilance, and the waking electroencephalogram in humans. Sleep 29: 161-168, 2006.

Ohayon M M, Smolensky M H and Roth T. Consequences of shiftworking on sleep duration, sleepiness, and sleep attacks. Chronobiol Int 27: 575-589, 2010.

Radloff L S. The CES-D Scale. Applied Psychological Measurement 1: 385-401, 1977.

Rahman S A, Marcu S, Shapiro C M, Brown T J and Casper R F. Spectral modulation attenuates molecular, endocrine, and neurobehavioral disruption induced by nocturnal light exposure. Am J Physiol Endocrinol Metab 300: E518-E527, 2011.

Rechtschaffen A and Kales A. A manual of standardized terminology, techniques and scoring system for sleep stages of human Subjects. Washington, D.C.: U.S. Government Printing Office, 1968.

Revell V L, Arendt J, Fogg L F and Skene D J. Alerting effects of light are sensitive to very short wavelengths. Neurosci Lett 399: 96-100, 2006.

Santhi N, Duffy J F, Horowitz T S and Czeisler C A. Scheduling of sleep/darkness affects the circadian phase of night shift workers. Neurosci Lett 384: 316-320, 2005.

Santhi N, Horowitz T S, Duffy J F, Czeisler C A. Acute sleep deprivation and circadian misalignment associated with transition onto the first night of work impairs visual selective attention. PLoS ONE 2:e1233, 2007.

Sasseville A, Benhaberou-Brun D, Fontaine C, Charon M C and Hebert M. Wearing blue-blockers in the morning could improve sleep of workers on a permanent night schedule: a pilot study. Chronobiol Int 26: 913-925, 2009.

Smith C S, Reilly C and Midkiff K. Evaluation of three circadian rhythm questionnaires with suggestions for an improved measure of morningness. J Appl Psychol 74: 728-738, 1989.

Smith M R, Fogg L F and Eastman C I. A compromise circadian phase position for permanent night work improves mood, fatigue, and performance. Sleep 32: 1481-1489, 2009.

Thapan K, Arendt J and Skene D J. An action spectrum for melatonin suppression: Evidence for a novel non-rod, non-cone photoreceptor system in humans. J Physiol 535: 261-267, 2001.

Thorne D R, Genser S G, Sing H C and Hegge F W. The Walter Reed performance assessment battery. Neurobehav Toxicol Teratol 7: 415-418, 1985.

Weissman M M, Sholomskas D, Pottenger M, Prusoff B A and Locke B Z. Assessing depressive symptoms in five psychiatric populations: a validation study. Am J Epidemiol 106: 203-214, 1977.

The invention claimed is:

1. A method for improving sleep performance in a subject, comprising:
 a) exposing the subject to an artificially lighted environment at night, wherein said exposing step causes one or more of the following in the subject:
 increased sleep onset latency;
 decreasing in total sleep time;
 increasing in wake after sleep onset; and
 increasing time in slow wave (stage 3 and 4) sleep and
 b) improving sleep performance after exposure to the artificially lighted environment by selectively substantially blocking retinal exposure of the subject to light of wavelengths less than 490 nm +/−5 nm during the night, wherein said improving of sleep performance comprises one or more of reducing sleep onset latency, increasing total sleep time, reducing wake after sleep onset, and increasing time in slow wave (stage 3 and 4) sleep.

2. The method of claim 1 wherein the method is practiced throughout the night.

3. The method of claim 1 wherein said substantial blocking of wavelengths of light is by means of an optical filter.

4. The method of claim 3 wherein the optical filter is incorporated into eyewear.

5. The method of claim 3 wherein the optical filter is incorporated into a light cover.

6. The method of claim 3 wherein the optical filter is incorporated into a coating for a light source.

7. The method of claim 3 wherein the optical filter is incorporated into a light source.

8. The method of claim 1 wherein the subject is exposed to a light source that excludes the blocked wavelengths of light.

9. The method of claim 8 wherein the light source is a display screen.

10. A method for improving sleep performance in a subject, comprising:
 a) exposing the subject to an artificially lighted environment at night, wherein said exposing step causes one or more of the following in the subject:
 increased sleep onset latency;
 decreasing in total sleep time;
 increasing in wake after sleep onset; and
 increasing time in slow wave (stage 3 and 4) sleep and
 b) improving sleep performance after exposure to the artificially lighted environment by selectively substantially blocking retinal exposure of the subject to light of wavelengths less than 480 nm +/−5 nm during the night, wherein said improving of sleep performance comprises one or more of reducing sleep onset latency, increasing total sleep time, reducing wake after sleep onset, and increasing time in slow wave (stage 3 and 4) sleep.

11. The method of claim 10 wherein the method is practiced throughout the night.

12. The method of claim 10 wherein the substantial blocking of wavelengths of light is by means of an optical filter.

13. The method of claim 12 wherein the optical filter is incorporated into eyewear.

14. The method of claim 12 wherein the optical filter is incorporated into a light cover.

15. The method of claim 12 wherein the optical filter is incorporated into a coating for a light source.

16. The method of claim 12 wherein the optical filter is incorporated into a light source.

17. The method of claim 10 wherein the subject is exposed to a light source that excludes the blocked wavelengths of light.

18. The method of claim 17 wherein the light source is a display screen.

19. A method for improving sleep performance in a subject, comprising:
   a) exposing a the subject to an artificially lighted environment at night, wherein said exposing step causes one or more of the following in the subject:
   increased sleep onset latency;
   decreasing in total sleep time;
   increasing in wake after sleep onset; and
   increasing time in slow wave (stage 3 and 4) sleep and
   b) improving sleep performance after exposure to the artificially lighted environment by selectively substantially blocking retinal exposure of the subject to light of wavelengths selected from the group consisting of between 410 nm +/−5 nm and 490 nm +/−5nm; between 415 nm +/−5 nm and 490 nm +/−5 nm; between 420 nm +/−5 nm and 490nm +/−5 nm; between 425 nm +/−5 nm and 490 nm +/−5 nm; between 410 nm +/−5 nm and 480 nm +/−5nm; between 415 nm +/−5 nm and 480 nm +/−5 nm; between 420 nm +/−5nm and 480nm +/−5 nm; and between 425 nm +/−5 nm and 480 nm +/−5 nm during the night, wherein said improving of sleep performance comprises one or more of reducing sleep onset latency, increasing total sleep time, reducing wake after sleep onset, and increasing time in slow wave (stage 3 and 4) sleep.

20. The method of claim 19 wherein substantial blocking of wavelengths of light is by means of an optical filter.

21. The method of claim 19 wherein the method is practiced throughout the night.

22. The method of claim 21 wherein the optical filter is incorporated into eyewear.

23. The method of claim 21 wherein the optical filter is incorporated into a light cover.

24. The method of claim 21 wherein the optical filter is incorporated into a coating for a light source.

25. The method of claim 21 wherein the optical filter is incorporated into a light source.

26. The method of claim 19 wherein the subject is exposed to a light source that excludes the blocked wavelengths of light.

27. The method of claim 26 wherein the light source is a display screen.

* * * * *